(12) United States Patent
Hildbrand et al.

(10) Patent No.: US 6,239,307 B1
(45) Date of Patent: May 29, 2001

(54) PROCESS FOR PREPARING CYANOACETIC ESTERS

(75) Inventors: Stefan Hildbrand, Visp; Paul Hanselmann, Brig-Glis, both of (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 09/500,634

(22) Filed: Feb. 9, 2000

Related U.S. Application Data

(60) Provisional application No. 60/145,997, filed on Jul. 29, 1999.

(30) Foreign Application Priority Data

Feb. 9, 1999 (EP) .................................. 99102286

(51) Int. Cl.$^7$ .................................. C07C 255/03
(52) U.S. Cl. .................................. 558/443
(58) Field of Search .................................. 558/443

(56) References Cited

U.S. PATENT DOCUMENTS 4,174,347    11/1979    Austermühle-Bertola .......... 260/464

OTHER PUBLICATIONS

Lhomet, Gerard, et al., C.R. Seances Acad. Sci., Ser. C, (1980), 290 (23), 445–7.

*Primary Examiner*—Floyd D. Higel
*Assistant Examiner*—Ebenezer Sackey
(74) *Attorney, Agent, or Firm*—Fisher, Christen & Sabol

(57) ABSTRACT

Cyanoacetic esters of the general formula:

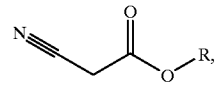

I in which R is $C_{1-10}$-alkyl, $C_{3-10}$-alkenyl or aryl-$C_{1-4}$alkyl, are prepared by the reaction of alkali metal cyanoacetates with the corresponding halides R—X, in which X is chlorine, bromine or iodine, in an aqueous/organic two-phase system in the presence of a phase-transfer catalyst.

16 Claims, No Drawings

PROCESS FOR PREPARING CYANOACETIC ESTERS

BACKGROUND OF THE INVENTION

This application claims benefit of provisional application No. 60/145,997 filed Jul. 29, 1999.

FIELD OF THE INVENTION

The invention relates to a process for preparing cyanoacetic esters of the general formula:

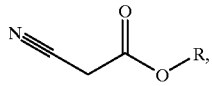

I in which R is $C_{1-10}$-alkyl, $C_{3-10}$-alkenyl or aryl-$C_{1-14}$-alkyl.

BACKGROUND ART

The customary synthesis of cyanoacetic esters is carried out by cyanidation of sodium chloroacetate in aqueous solution, followed by an acid-catalyzed esterification with the appropriate alcohol, where the water formed is distilled off azeotropically. An essential disadvantage of this two-step process is the fact that the water has to be removed after cyanidation, since the subsequent esterification is only possible under substantially water-free conditions. On an industrial scale, that is usually carried out by evaporating the water.

Since the sodium cyanoacetate, which is formed as an intermediate, is moreover highly water-soluble, a method for its esterification in water as the solvent is desirable.

BROAD DESCRIPTION OF THE INVENTION

Accordingly, an object of the invention is to provide a process where the aqueous solution of sodium cyanoacetate, which is obtained after cyanidation, can be esterified directly. According to the invention, the object is achieved by the process of the invention.

It has been found that cyanoacetic esters of the general formula:

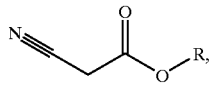

I in which R is $C_{1-10}$-alkyl, $C_{3-10}$-alkenyl or aryl-$C_{1-4}$-alkyl can be prepared by reacting an alkali metal cyanoacetate in an aqueous/organic two-phase system in the presence of a phase-transfer catalyst with a halide of the general formula R-X (II), in which R is as defined above and X is chlorine, bromine or iodine. The organic phase used can be the halide (II) by itself or in a mixture with an organic solvent.

Herein, $C_{1-10}$-alkyl is to be understood as any linear or branched primary, secondary or tertiary alkyl group having 1 to 10 carbon atoms, in particular groups such as methyl, ethyl, propyl, isopropyl, butyl, isobutyl, sec-butyl, tert-butyl, pentyl, hexyl, heptyl, octyl, nonyl or decyl.

Herein, $C_{3-10}$-alkenyl is to be understood as the corresponding groups having 3 to 10 carbon atoms and at least one C=C double bond, where the double bond is advantageously separated from the free valency by at least one saturated carbon atom. These $C_{3-10}$-alkenyls include, in particular, groups such as allyl, methallyl, but-2-enyl (crotyl), but-3-enyl, etc.

Herein, aryl-$C_{1-4}$-alkyl is to be understood as, in particular, phenyl-substituted $C_{1-4}$-alkyl groups, such as, benzyl, phenethyl or 3-phenylpropyl, where the phenyl group can also contain one or more identical or different substituents, such as, $C_{1-4}$-alkyl, $C_{1-4}$-alkoxy or halogen.

The alkali metal cyanoacetate which is preferably used is sodium cyanoacetate. The sodium cyanoacetate is particularly preferably employed in the form of the aqueous solution obtained in the reaction of sodium chloroacetate with sodium cyanide.

X is preferably chlorine or bromine.

The phase-transfer catalyst which is preferably employed is a quaternary ammonium salt. Particularly preferred quaternary ammonium salts are the tetra-n-$C_{4-10}$-alkylammonium, benzyltri-n-$C_{1-8}$-alkylammonium or methyltri-n-$C_{4-10}$-alkylammonium halides, in particular the chlorides and bromides.

Preference is also given to using tert-butyl methyl ether or chlorobenzene as the solvent in the organic phase.

DETAILED DESCRIPTION OF THE INVENTION

The examples below illustrate the practice of the process according to the invention without limiting it. All reactions were carried out in an autoclave having an internal volume of about 250 ml. The yield was determined by gas chromatography with the aid of an internal standard.

EXAMPLE 1

Methyl Cyanoacetate 10.0 g (9.9 equivalents, 0.20 mol) of methyl chloride was introduced into a mixture of 1.70 g (0.02 mol) of cyanoacetic acid, 0.8 g (0.2 mol) of sodium hydroxide and 0.64 g (2.0 mmol) of tetrabutylammonium bromide in 15 ml of tert-butyl methyl ether/water 2:1. The reaction mixture was heated to an internal temperature of 100° C. (oil bath temperature 110° C.) over a period of 30 minutes, during which time the pressure in the autoclave increased from 4 to 10 bar. After 3.5 h at 100° C., the autoclave was cooled and vented. The pH of the aqueous phase was adjusted from 2.9 to 5.9 using 3.10 g of 1 M aqueous sodium hydroxide solution, the organic phase was separated off and the aqueous phase was extracted with tert-butyl methyl ether (2×6 ml). The combined organic phases was dried with sodium sulfate, admixed with dimethyl succinate (as an internal standard) and analyzed by gas chromatography. 1.36 g (68 percent) of methyl cyanoacetate was obtained.

Comparative Example 1

Methyl Cyanoacetate

The method described in Example 1 was repeated, but without the addition of tetrabutylammonium bromide. The yield of methyl cyanoacetate was only 13 percent.

EXAMPLE 2

Ethyl Cyanoacetate

A mixture of 1.70 g (0.02 mol) of cyanoacetic acid, 0.8 g (0.02 mol) of sodium hydroxide, 10.90 g (0.10 mol, 5 equivalents) of ethyl bromide and 0.64 g (2.0 mmol) of tetrabutylammonium bromide in 15 ml of chlorobenzene/ water (2:1) was heated to an internal temperature of 100° C. over a period of 30 min and stirred at 100° C. (oil bath temperature 110° C.) for 3.5 h. The reaction mixture was then cooled, the phases were separated and the aqueous phase (pH=6.85) was extracted with tert-butyl methyl ether (2×5 ml). The combined organic phases was dried with sodium sulfate, admixed with dimethyl succinate (as an internal standard) and analyzed by gas chromatography. 1.46 g (65 percent) of ethyl cyanoacetate was obtained.

EXAMPLE 3

Benzyl Cyanoacetate

A mixture of 1.7 g (0.02 mol) of cyanoacetic acid, 0.8 g (0.02 mol) of sodium hydroxide, 7.60 g (0.06 mol, 3 equivalents) of benzyl chloride and 0.64 g (2.0 mmol) of tetrabutylammonium bromide in 15 ml of tert-butyl methyl ether/water (v:v=2:1 ) was stirred at 100° C. (oil bath temperature 110° C.) for 3 h. The pH of the aqueous phase was then adjusted from 0.2 to 6.3 using 3.15 g of 1 M aqueous sodium hydroxide solution, the organic phase was separated off and the aqueous phase was extracted with tert-butyl methyl ether (2×5 ml). The combined organic phases was dried with sodium sulfate and analyzed by gas chromatography. 2.45 g (70 percent) of benzyl cyanoacetate was obtained.

What is claimed is:

1. A process for preparing a cyanoacetic ester of formula:

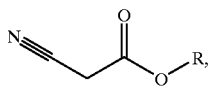

I in which R is $C_{1-10}$-alkyl, $C_{3-10}$-alkenyl or aryl-$C_{1-4}$-alkyl, comprising reacting an alkali metal cyanoacetate in an aqueous/organic two-phase system in the presence of a phase-transfer catalyst with a halide of formula R—X (II), in which R is as defined above and X is chlorine, bromine or iodine.

2. The process according to claim 1, wherein the alkali metal cyanoacetate is sodium cyanoacetate.

3. The process according to claim 2, wherein the sodium cyanoacetate is used in the form of the aqueous solution obtained in the reaction of sodium chloroacetate with sodium cyanide.

4. The process according to claim 3, wherein X is chlorine or bromine.

5. The process according to claim 4, wherein the phase-transfer catalyst is a quaternary ammonium salt.

6. The process according to claim 5, wherein the quaternary ammonium salt is a tetra-n-$C_{4-10}$-alkylammonium halide, a benzyltri-n-$C_{1-8}$-alkylammonium halide or a methyltri-n-$C_{4-10}$-alkylammonium halide.

7. The process according to claim 6, wherein halide is chloride or bromide.

8. The process according to claim 6, wherein the organic phase comprises tert-butyl methyl ether or chlorobenzene as a solvent.

9. The process according to claim 1, wherein X is chlorine or bromine.

10. The process according to claim 1, wherein the phase-transfer catalyst is a quaternary ammonium salt.

11. The process according to claim 10, wherein the quaternary ammonium salt is a tetra-n-$C_{4-10}$-alkylammonium halide, a benzyltri-n-$C_{1-8}$-alkylammonium halide or a methyltri-n-$C_{4-10}$-alkylammonium halide.

12. The process according to claim 11, wherein halide is chloride or bromide.

13. The process according to claim 1, wherein the organic phase comprises tert-butyl methyl ether or chlorobenzene as a solvent.

14. A process for preparing a cyanoacetic ester of formula:

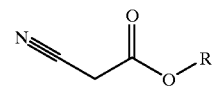

I in which R is $C_{1-10}$-alkyl, $C_{3-10}$-alkenyl or aryl-$C_{1-4}$-alkyl, comprising reacting an alkali metal cyanoacetate in an aqueous/organic two-phase system in the presence of a phase-transfer catalyst with a halide of formula R—X (II), in which R is as defined above and X is chlorine, bromine, or iodine, the organic phase comprising the halide of formula R—X (II).

15. The process according to claim 14 wherein, after the, reaction, the organic phase and the aqueous phase are separated, the aqueous phase is extracted to remove organics in the aqueous phase, and the organic phase and the extracted organics are combined.

16. The process according to claim 1 wherein, after the reaction, the organic phase and the aqueous phase are separated, the aqueous phase is extracted, and the organic phase and the extracted organics are combined.

* * * * *